United States Patent
Green et al.

(10) Patent No.: US 9,734,995 B2
(45) Date of Patent: Aug. 15, 2017

(54) TIME OF FLIGHT QUANTITATION USING ALTERNATIVE CHARACTERISTIC IONS

(71) Applicant: Micromass UK Limited, Wilmslow (GB)

(72) Inventors: Martin Raymond Green, Bowdon (GB); Gareth Rhys Jones, Altrincham (GB); Michael Raymond Morris, Glossop (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 290 days.

(21) Appl. No.: 14/385,788

(22) PCT Filed: Mar. 6, 2013

(86) PCT No.: PCT/GB2013/050553
§ 371 (c)(1),
(2) Date: Sep. 17, 2014

(87) PCT Pub. No.: WO2013/140127
PCT Pub. Date: Sep. 26, 2013

(65) Prior Publication Data
US 2015/0041635 A1    Feb. 12, 2015

(30) Foreign Application Priority Data
Mar. 19, 2012   (GB) .................................. 1204723.9

(51) Int. Cl.
*H01J 49/00* (2006.01)
*G01N 27/62* (2006.01)
(Continued)

(52) U.S. Cl.
CPC ........ *H01J 49/0036* (2013.01); *G01N 27/622* (2013.01); *H01J 49/26* (2013.01); *H01J 49/40* (2013.01)

(58) Field of Classification Search
CPC .. H01J 49/005; H01J 49/0031; H01J 49/0045; G01N 33/6848; G01N 30/7206; G01N 30/7233
(Continued)

(56) References Cited

U.S. PATENT DOCUMENTS

| | | |
|---|---|---|
| 4,008,388 A | 2/1977 | McLafferty et al. |
| 5,202,562 A | 4/1993 | Koga et al. |

(Continued)

OTHER PUBLICATIONS

Keshishian, et al ("Quantitative Multiplexed Assays for Low Abundance Proteins in Plasma by Targeted Mass Spectrometry and Stable Isotope Dilution," Mol. Cell Proteomics, Dec. 2007; 6(12): 2212-2229).*

*Primary Examiner* — Michael Maskell
(74) *Attorney, Agent, or Firm* — Diedericks & Whitelaw, PLC

(57) ABSTRACT

A method of mass spectrometry is disclosed wherein the intensity of an analyte is determined by determining the intensity of first characteristic fragment ions when the intensity of the first characteristic fragment ions is within a first intensity range corresponding to the detection or unsaturated range of an ion detector. However, when the intensity of the first characteristic fragment ions is outside of the first intensity range so that the ion detector would saturate then the intensity of the analyte is determined by determining the intensity of second different characteristic fragment ions.

30 Claims, 9 Drawing Sheets

(51) Int. Cl.
*H01J 49/26* (2006.01)
*H01J 49/40* (2006.01)

(58) Field of Classification Search
USPC .................................. 250/281, 282
See application file for complete search history.

(56) References Cited

U.S. PATENT DOCUMENTS

| | | |
|---|---|---|
| 6,974,951 B1 | 12/2005 | Kingston |
| 7,323,682 B2 | 1/2008 | McCauley et al. |
| 7,348,553 B2 | 3/2008 | Wang et al. |
| 7,588,906 B2 | 9/2009 | Brueggemeier et al. |
| 8,067,728 B2 | 11/2011 | Thomson et al. |
| 8,073,635 B2 | 12/2011 | Thomson et al. |
| 8,367,414 B2 | 2/2013 | Jasper |
| 2002/0037532 A1* | 3/2002 | Regnier ............. G01N 33/6803 435/7.1 |
| 2005/0063864 A1* | 3/2005 | Sano ................ G01N 33/6848 422/68.1 |
| 2006/0169883 A1* | 8/2006 | Wang ..................... B01D 59/44 250/282 |
| 2006/0255263 A1* | 11/2006 | Ishimaru ............ G01N 30/8675 250/288 |
| 2008/0052011 A1 | 2/2008 | Wang et al. |
| 2014/0299762 A1 | 10/2014 | Mukaibatake |

\* cited by examiner

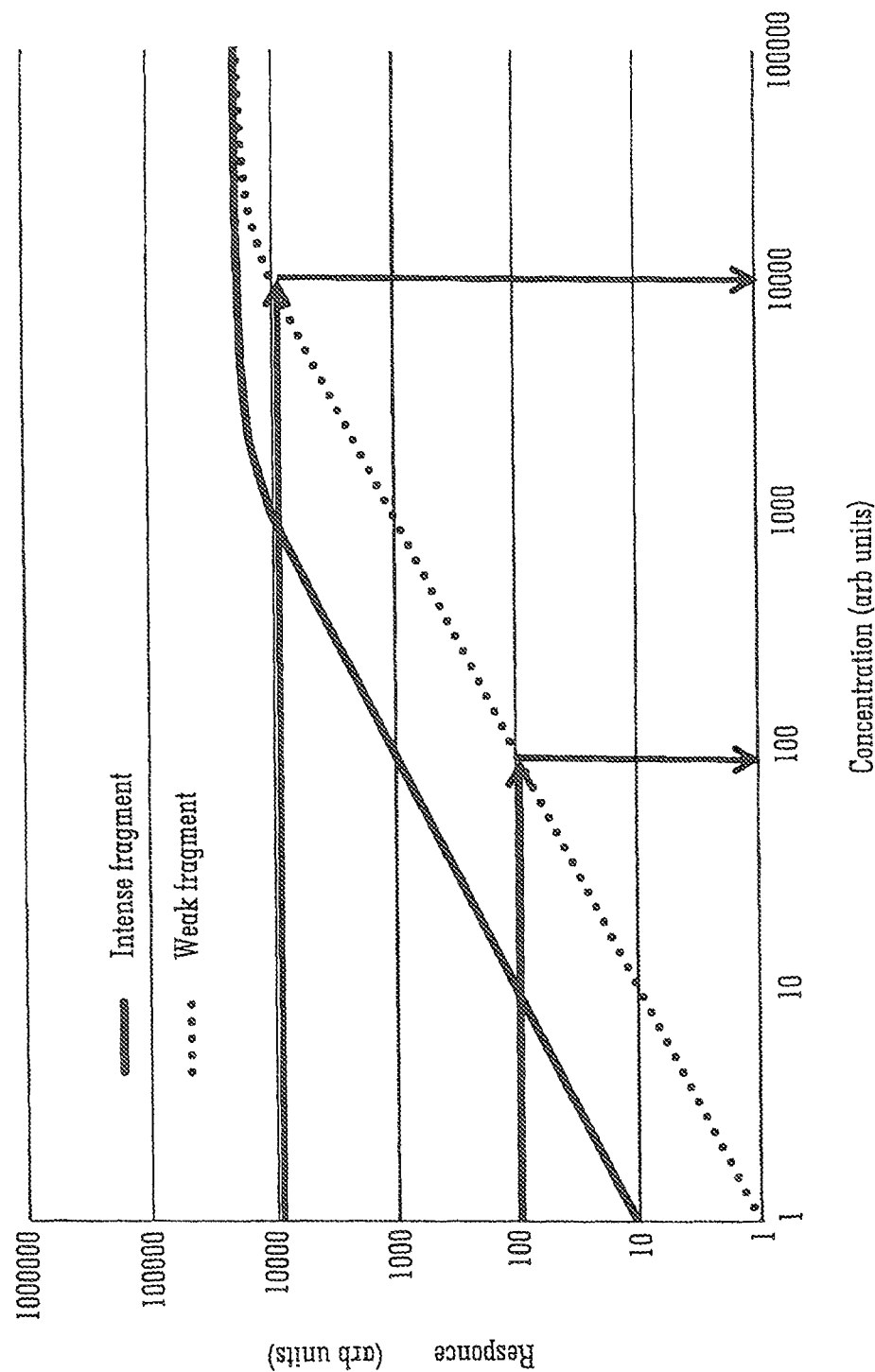

| Ranked Detection Probability | Isotopes of Ratio | | Ratio Acceptable? | | |
| --- | --- | --- | --- | --- | --- |
| | Primary | Secondary | Sample A | Sample B | Sample C |
| 1 | 3 | 1 | Yes | Yes | |
| 2 | 3 | 5 | Yes | Yes | |
| 3 | 1 | 5 | Yes | Yes | |
| 4 | 3 | 4 | | Yes | |
| 5 | 3 | 7 | | Yes | |
| 6 | 3 | 2 | | Yes | |
| 7 | 1 | 4 | | Yes | |
| 8 | 3 | 6 | | Yes | |
| 9 | 1 | 7 | | Yes | |
| 10 | 1 | 2 | | Yes | |
| 11 | 1 | 6 | | Yes | |
| 12 | 5 | 4 | | Yes | |
| 13 | 5 | 7 | | Yes | |
| 14 | 5 | 2 | | Yes | |
| 15 | 5 | 6 | | Yes | |
| 16 | 3 | 8 | | Yes | |
| 17 | 3 | 9 | | Yes | |
| 18 | 1 | 8 | | Yes | |
| 19 | 1 | 9 | | Yes | |
| 20 | 5 | 8 | | Yes | |
| 21 | 5 | 9 | | Yes | |
| 22 | 4 | 7 | | Yes | Yes |
| 23 | 4 | 2 | | Yes | Yes |
| 24 | 7 | 2 | | Yes | Yes |
| 25 | 4 | 6 | | Yes | Yes |
| 26 | 3 | 10 | | Yes | |
| 27 | 7 | 6 | | Yes | Yes |
| 28 | 2 | 6 | | Yes | Yes |
| 29 | 1 | 10 | | Yes | |
| 30 | 5 | 10 | | Yes | Yes |
| 31 | 4 | 8 | | Yes | Yes |
| 32 | 4 | 9 | | Yes | Yes |
| 33 | 7 | 8 | | Yes | Yes |
| 34 | 2 | 8 | | Yes | Yes |
| 35 | 7 | 9 | | Yes | Yes |
| 36 | 2 | 9 | | Yes | Yes |
| 37 | 6 | 8 | | Yes | Yes |
| 38 | 6 | 9 | | Yes | |
| 39 | 4 | 10 | | Yes | |
| 40 | 7 | 10 | | Yes | |
| 41 | 2 | 10 | | Yes | |
| 42 | 6 | 10 | | Yes | |
| 43 | 8 | 9 | | Yes | Yes |
| 44 | 8 | 10 | | Yes | |
| 45 | 9 | 10 | | Yes | |

FIG. 7

TIME OF FLIGHT QUANTITATION USING ALTERNATIVE CHARACTERISTIC IONS

CROSS-REFERENCE TO RELATED APPLICATION

This application is the National Stage of International Application No. PCT/GB2013/050553 filed 6 Mar. 2013, which claims priority from and the benefit of United Kingdom Patent Application No. 1204723.9 filed on 19 Mar. 2012. The entire contents of this application is incorporated herein by reference.

BACKGROUND OF THE PRESENT INVENTION

The present invention relates to a method of mass spectrometry and a mass spectrometer.

Historically, Multiple Reaction Monitoring ("MRM") experiments to select and quantitate specific ions in a complex sample have been carried out using tandem quadrupole instruments wherein a first analytical quadrupole mass filter is arranged to select or isolate specific parent or precursor ions of interest. A fragmentation device is located downstream of the first analytical quadrupole mass filter and is arranged to fragment the parent or precursor ions of interest to form fragment ions. A second analytical quadrupole mass analyser located downstream of the fragmentation device is then arranged to mass analyse the characteristic fragment ions.

Desired parent or precursor ion to fragment ion transitions are determined via a method development stage wherein the transitions are arranged as a function of elution time from a chromatographic device such as a Liquid Chromatography ("LC"), Gas Chromatography ("GC") or Capillary Electrophoresis ("CE") device. In some applications multiple transitions per parent or precursor ion may be arranged in order to give an added level of confidence that the measured component is actually the correct one.

Recently, it has become apparent that the specificity or selectivity of tandem quadrupole MRM experiments, particularly in relation to complex mixtures such as those seen in proteomics, is insufficient in some circumstances.

In order to address this problem it is known to perform high resolution MRM experiments using a mass spectrometer wherein the second analytical quadrupole mass analyser is replaced with a higher resolution mass analyser such as an Orbitrap® mass analyser or an orthogonal acceleration Time of Flight mass analyser.

FIG. 1 shows a current state of the art mass spectrometer that may be utilised to perform high resolution MRM experiments.

It is known to provide a quadrupole mass filter 2 in conjunction with an orthogonal acceleration Time of Flight mass analyser 4 as shown in FIG. 1 wherein parent or precursor ions are isolated or selected by the quadrupole rod set mass filter 2 and are then subsequently fragmented in a gas cell 3. The resulting characteristic fragment ions are then mass analysed using the high resolution orthogonal acceleration Time of Flight mass analyser 4.

Using a high resolution orthogonal acceleration Time of Flight mass analyser 4 has several advantages compared with using a resolving analytical quadrupole mass analyser.

Firstly, the higher resolution orthogonal acceleration Time of Flight mass analyser 4 reduces the likelihood of an interference effecting the quantitative measurement of the characteristic fragment ions.

Secondly, the orthogonal acceleration Time of Flight mass analyser 4 inherently has a high mass measurement accuracy of the order of 1-3 ppm RMS. This mass accuracy can be used to improve the specificity of the transition.

Thirdly, the orthogonal acceleration Time of Flight mass analyser 4, by virtue of the fact that it is a mass spectrometer as opposed to a mass filter, analyses multiple ions (characteristic fragment ions in this case) simultaneously and with a high duty cycle. The resulting full mass spectral data contains multiple characteristic fragment ions for the same parent or precursor ions again improving the specificity. Multiple isotopes are also included in the full mass spectrum again improving specificity.

Despite these benefits, current state of the art mass spectrometers similar to the arrangement shown in FIG. 1 nonetheless suffer from some certain problems.

One problem with current state of the art mass spectrometers is that they suffer from some loss in duty cycle as a result of mass analysing ions using an orthogonal acceleration Time of Flight mass analyser 4.

It is known to seek partially to compensate for this by either operating the Time of Flight mass analyser 4 in an Enhanced Duty Cycle ("EDC") mode of operation wherein the mass range of ions analysed at any point in time is reduced or alternatively by operating the Time of Flight mass analyser 4 in a High Duty Cycle ("HDC") mode of operation or a scanwave/zeno lens mode of operation wherein the dynamic range is reduced.

Typically, the dynamic range of the ion detection system used in conjunction with an orthogonal acceleration Time of Flight mass analyser 4 is inferior to that of a quadrupole rod set mass analyser due to the high digitisation rate requirements of an orthogonal acceleration Time of Flight mass analyser 4.

Current state of the art Time of Flight mass analysers employing Analogue to Digital Converters ("ADC") exhibit significant improvements compared with previous mass spectrometers that used Time to Digital Convertors ("TDC"). Future developments in digitations rates and/or multiple gain stage ADCs promise further improvements.

It is known to seek to improve the dynamic range of an orthogonal acceleration Time of Flight mass analyser by means of Programmable Dynamic Range Enhancements ("pDRE") and Automatic Gain Control ("AGC"). However, these approaches usually involve a loss in sensitivity and/or duty cycle.

State of the art instruments that employ quantitative acquisitions use the same ion or ions for quantification irrespective of the nature of the data.

It is known to calibrate a mass spectrometer by injecting a first calibration sample having a known (low) concentration of calibrant and then measuring the low intensity signal response. Second and further calibration samples having progressively higher calibrant concentrations are then sequentially injected or other introduced into the mass spectrometer and increasingly higher signal intensities or responses are observed.

At a certain point the ion detector will start to saturate and the detector response will not increase further. This gives an indication of the upper limit of quantitation and provides an upper limit to the effective dynamic range of the mass spectrometer.

It is desired to provide a mass spectrometer and a method of mass spectrometry having an improved dynamic range.

SUMMARY OF THE PRESENT INVENTION

According to an aspect of the present invention there is provided a method of mass spectrometry comprising:

determining the intensity of (or quantitating) an analyte by determining the intensity of first characteristic ions when the intensity of the first ions is within a first range; and determining the intensity of (or quantitating) the analyte by determining the intensity of second different characteristic ions when the intensity of the first ions is outside of the first range.

It should be understood that the first and second characteristic ions relate to e.g. different species of fragment ions and/or different isotopes of the analyte and that the first and second characteristic ions should not therefore be construed as merely relating to two populations of the same analyte ions at different intensities. Accordingly, the mass to charge ratio and/or chemical structure and/or number of neutrons and/or other physico-chemical property of the first and second characteristic ions is preferably different.

The first characteristic ions preferably comprise fragment, product or adduct ions derived from the analyte.

According to another embodiment the first characteristic ions may comprise one or more first isotopes of the analyte.

The second characteristic ions preferably comprise fragment, product or adduct ions derived from the analyte.

According to another embodiment the second characteristic ions may comprise one or more second isotopes of the analyte.

The first range (e.g. an ion detector response or intensity range) preferably substantially corresponds with the detection or unsaturated range of an ion detector.

When the intensity of the first characteristic ions is outside of the first range, the intensity of the second different characteristic ions is preferably still substantially within the detection or unsaturated range of the ion detector.

The method preferably further comprises determining one or more isotope ratios of the analyte in order to confirm the identity of the analyte and/or to identify the analyte.

The step of determining one or more isotope ratios of the analyte preferably comprises:

determining one or more first isotope ratios by analysing a first sample comprising a first concentration of the analyte; and determining one or more second different isotope ratios by analysing a second different sample comprising a second different concentration of the analyte.

The method preferably further comprises controlling an instrument parameter of a mass spectrometer based upon a determination of the intensity or other property of the first characteristic ions and/or the intensity or other property of the second characteristic ions.

The instrument parameter preferably comprises: (i) a collision or fragmentation energy; (ii) an ionisation efficiency; (iii) an on transmission efficiency; or (iv) an ion detector gain.

The method preferably further comprises separating parent or fragment ions according to a physico-chemical property.

The physico-chemical property preferably comprises on mobility, differential on mobility, mass, mass to charge ratio or time of flight.

The method preferably comprises a method of Multiple Reaction Monitoring ("MRM").

According to the preferred embodiment parent analyte ions are preferably selected or isolated by a mass filter. The mass filter preferably comprises a quadrupole rod set mass filter.

Parent analyte ions selected or isolated by the mass filter are preferably fragmented or reacted to form the first characteristic ions and/or the second characteristic ions.

The step of determining the intensity of the first characteristic ions preferably comprises mass analysing the first characteristic ions.

The step of determining the intensity of the second characteristic ions preferably comprises mass analysing the second characteristic ions.

The step of mass analysing the first and/or second characteristic ions preferably comprises mass analysing the first and/or second characteristic ions using an axial acceleration or orthogonal acceleration Time of Flight mass analyser.

The first and second characteristic ions preferably have different masses and/or different mass to charge ratios and/or different chemical structures and/or different number of neutrons and/or one more different physicochemical properties.

According to another aspect of the present invention there is provided a mass spectrometer comprising:

a control system arranged and adapted:

(i) to determine the intensity of an analyte by determining the intensity of first characteristic ions when the intensity of the first characteristic ions is within a first range; and (ii) to determine the intensity of the analyte by determining the intensity of second different characteristic ions when the intensity of the first characteristic ions is outside of the first range.

The mass spectrometer preferably further comprises a separator for separating parent or fragment ions according to a physico-chemical property.

The separator preferably comprises an ion mobility, differential ion mobility, mass, mass to charge ratio or time of flight separator.

The control system is preferably arranged and adapted to perform a Multiple Reaction Monitoring ("MRM") analysis.

The mass spectrometer preferably further comprises a mass filter for selecting or isolating parent analyte ions.

The mass spectrometer preferably further comprises a fragmentation or reaction device wherein the parent analyte ions selected or isolated by the mass filter are preferably fragmented or reacted, in use, within the fragmentation or reaction device to form the first characteristic ions and/or the second characteristic ions.

The mass spectrometer preferably further comprises a mass analyser for mass analysing the first and/or second characteristic ions and determining the intensity of the first and/or second characteristic ions.

The mass analyser preferably comprises an axial acceleration or orthogonal acceleration Time of Flight mass analyser.

The first and second characteristic ions preferably have different masses and/or different mass to charge ratios and/or different chemical structures and/or different number of neutrons and/or one more different physico-chemical properties.

According to another aspect of the present invention there is provided a method of mass spectrometry comprising:

determining one or more first isotope ratios by analysing a first sample comprising a first concentration of an analyte; and determining one or more second different isotope ratios by analysing a second different sample comprising a second different concentration of the analyte.

The one or more first isotope ratios and/or the one or more second isotope ratios are preferably used to confirm the identity of the analyte and/or to identify the analyte.

The step of determining the one or more first and/or second isotope ratios is preferably performed using an axial acceleration or an orthogonal acceleration Time of Flight mass analyser.

According to another aspect of the present invention there is provided a mass spectrometer comprising:

a control system arranged and adapted:

(i) to determine one or more first isotope ratios by analysing a first sample comprising a first concentration of an analyte; and (ii) to determine one or more second different isotope ratios by analysing a second different sample comprising a second different concentration of the analyte.

The preferred embodiment relates to improving the dynamic range of a mass spectrometer and is particularly useful for high peak capacity tandem instruments such as those including both an ion Mobility Separator ("IMS") device and a Time of Flight mass analyser.

Improved Time of Flight quantitation according to an embodiment of the present invention by using alternative characteristic fragment ions is a new mode of operation for existing instrument geometries and future novel instrument geometries.

The preferred embodiment provides the capability to improve the dynamic range of Time of Flight instruments operating in quantitative modes by intelligently determining which characteristic ions to use for quantitation.

The preferred approach is particularly useful in geometries employing additional separations such as ion mobility.

BRIEF DESCRIPTION OF THE DRAWINGS

Various embodiments of the present invention together with an arrangement given for illustrative purposes only, will now be described, by way of example only and with reference to the accompanying drawings in which:

FIG. 4 illustrates the dynamic range for the weakest intensity species of characteristic fragment ion and FIG. 4A shows a response versus concentration curve for an ADC based detection system and shows the dynamic range for the weakest intensity species of characteristic fragment ions;

FIG. 7 shows a table wherein the 45 unique isotopic ratios corresponding to the ten isotopes as shown in FIG. 6 are ranked in order of their detection probability.

DETAILED DESCRIPTION OF PREFERRED EMBODIMENTS

A preferred embodiment of the present invention will now be described in more detail with reference to FIG. 2. The preferred embodiment of the present invention seeks to improve the dynamic range of a detector system of a mass spectrometer. The mass spectrometer preferably comprises an ion mobility separator 5, a quadrupole mass filter 2, a gas cell 3 and an orthogonal acceleration Time of Flight mass analyser 4.

Figure 1:
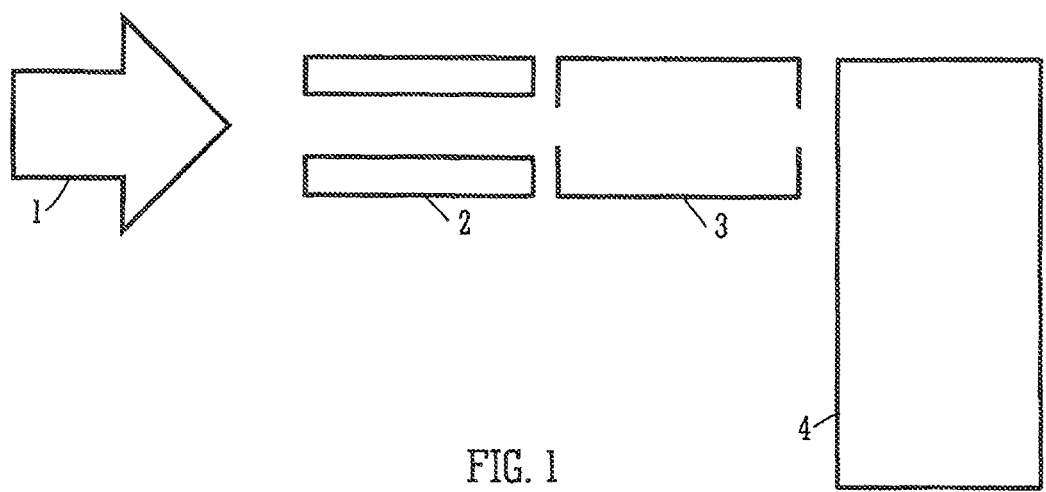
FIG. 1 shows a known quadrupole-Time of Flight mass analyser which may be used to perform high resolution MRM analyses.
Figure 2:
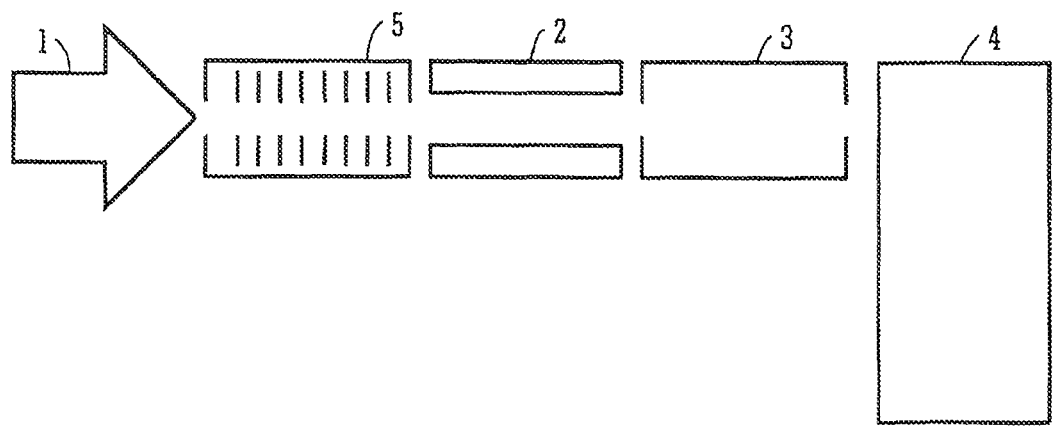
FIG. 2 shows a IMS-quadrupole-Time of Flight mass analyser according to an embodiment of the present invention.

The benefits of improving the dynamic range of an orthogonal acceleration Time of Flight mass analyser 4 according to the preferred embodiment will become apparent when considering instrument geometries which employ multiple separation devices such as an IMS-Quadrupole-Time of Right mass spectrometer as shown in FIG. 2. In this geometry the duty cycle and specificity of MRM experiments can be significantly improved compared with known mass spectrometers as shown in FIG. 1.

The present invention also extends to other geometries wherein, for example, the order of the IMS device 5 and the quadrupole mass filter 2 may be reversed from that shown in FIG. 2. For example, according to a less preferred embodiment a Quadrupole-IMS-Time of Flight mass spectrometer may be provided and can also provide improved duty cycle and specificity of fragment ions.

According to the preferred embodiment duty cycle and specificity improvements are achieved by separation and compression of ion signals in time. This compression places higher demands on the dynamic range of the acquisition systems of orthogonal acceleration Time of Flight mass spectrometers 4.

The ability to be able to improve the dynamic range of a Time of Flight mass spectrometer 4 according to the preferred embodiment is particularly advantageous.

The preferred embodiment of the present invention seeks to improve the dynamic range of MRM experiments by monitoring and measuring a wide range of characteristic fragment, product or other ions for each parent or precursor ion during a method development stage.

Calibration curves of response versus sample concentration are determined for the range of characteristic fragment, product or other ions. Choice of which calibration curve to use is based on the analyte data acquired.

Multiple calibration curves may be used or combined within a single experiment for a single component if the analyte data indicates a benefit. The choice to switch calibration curves may be done in real time or as part of a post acquisition approach.

Figure 3:
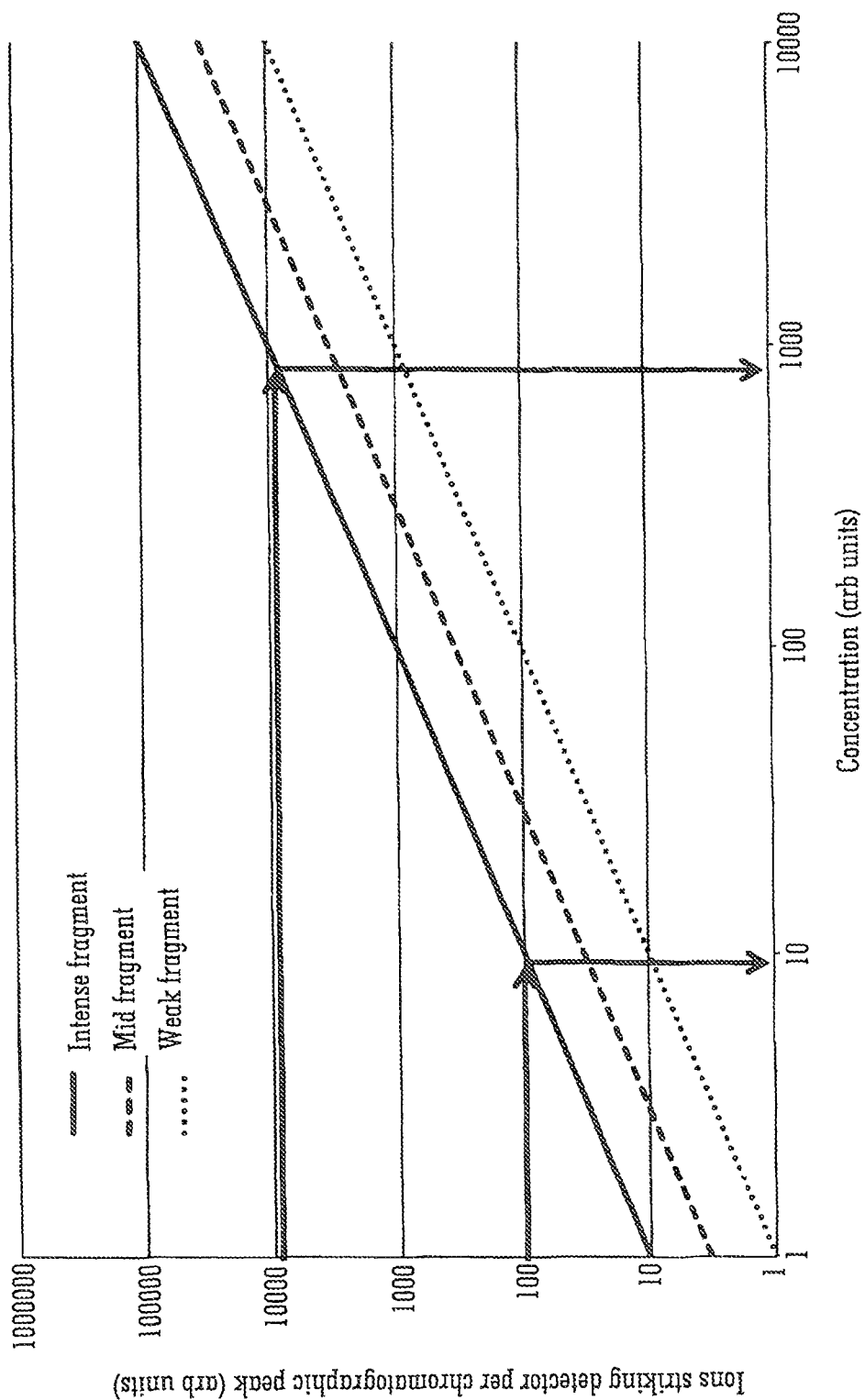
FIG. 3 shows three transitions and illustrates the dynamic range for the most intense species of characteristic fragment ion and FIG. 3A shows a response versus concentration curve for an ADC based detection system and shows the dynamic range for the most intense species of characteristic fragment ions.
Figure 4:
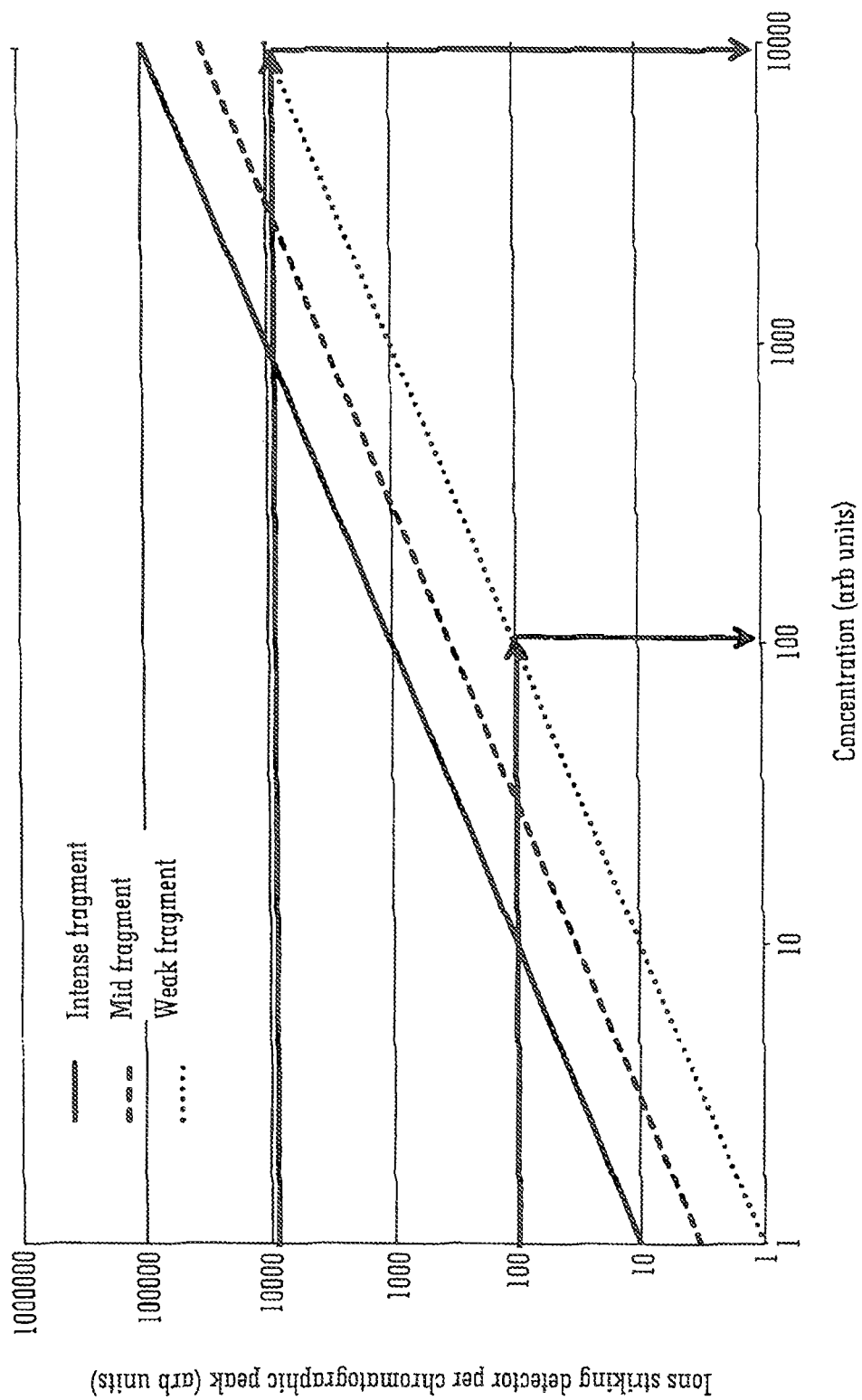
Figure 5:
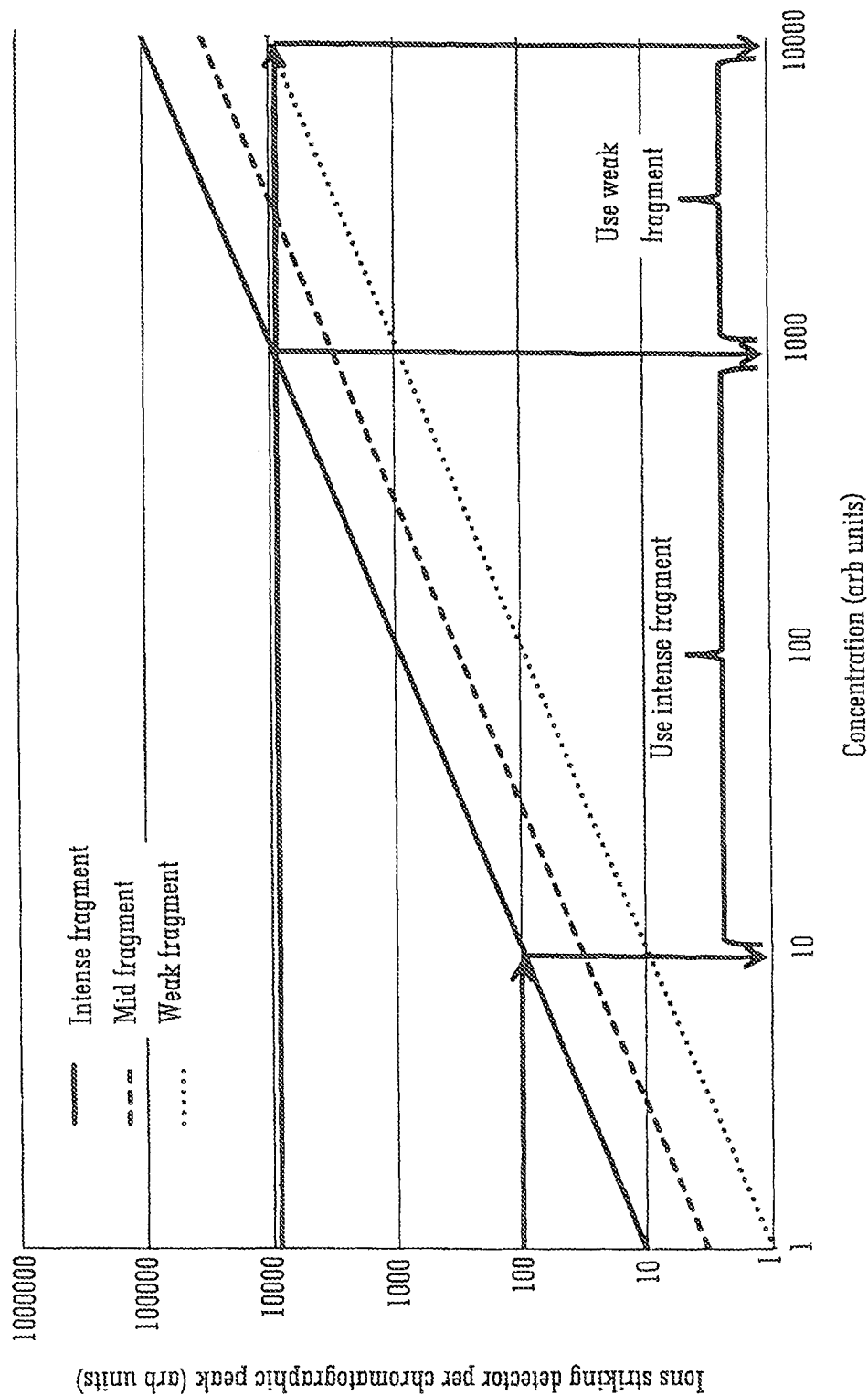
FIG. 5 illustrates an embodiment of the present invention wherein a ×10 increase in the dynamic range is obtained by using the most intense species of characteristic fragment ions at low and moderate analyte sample concentrations to quantitate an analyte and using the weakest intensity species of characteristic fragment ions at high analyte sample concentrations to quantitate the analyte and FIG. 5A shows a response versus concentration curve for an ADC based detection system and shows how the dynamic range may be extended according to an embodiment of the present invention.

FIGS. 3-5 illustrate in more detail how this approach may be utilised to improve the dynamic range of a mass spectrometer according to an embodiment of the present invention.

The data shown in FIG. 3 represents three transitions i.e. three different characteristic fragment ions all of which result from the fragmentation of the same species of parent or precursor ion. The data is acquired using a known Quadrupole-Time of Flight mass spectrometer as shown in FIG. 1.

In this example the most intense species of characteristic fragment ions has an intensity which is ×10 greater than that of the weakest intensity species of characteristic fragment ions. This difference appears as an offset in the log—log plot shown in FIG. 3.

If an arbitrary minimum number of ions (e.g. 100) is required as being necessary for quantification and an arbitrary number of ions (e.g. 10,000) ions is chosen as being the upper knit above which ion detector saturation will occur, then the dynamic range may be defined as 100:1 or two orders of magnitude for this example. The dynamic range for the most intense species of fragment ions is indicated by arrows in FIG. 3.

Figure 3A:
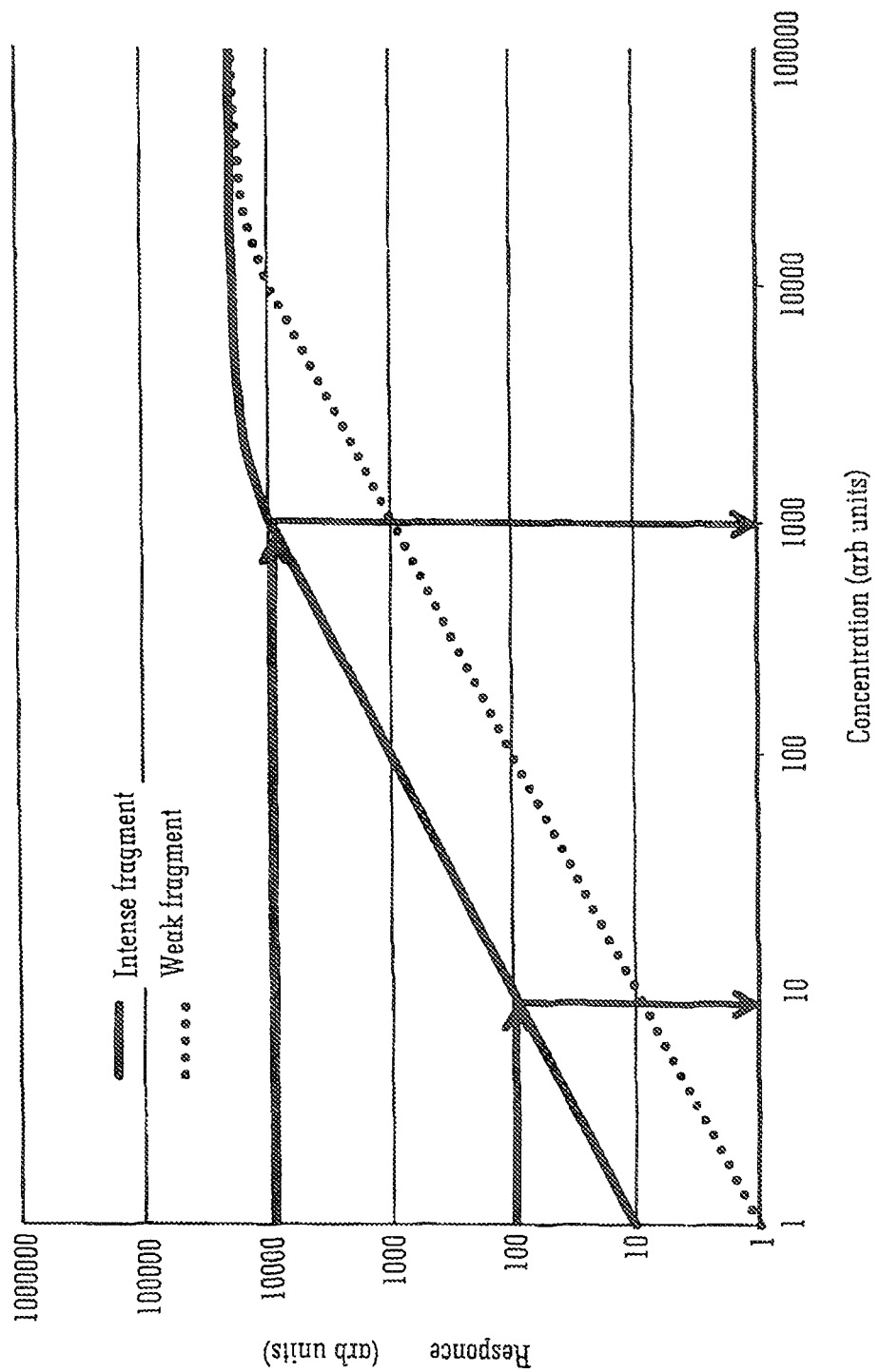

Considering an ADC based detection system then the response versus concentration curve for FIG. 3 would be as shown in FIG. 3A.

If a response of 100 arbitrary units is defined as the lower limit for quantification, mass accuracy or as the lower detection limit, then the response is linear from that point over two orders of magnitude in concentration until the response starts to saturate at high concentrations.

Applying the same approach to the weakest intensity species of characteristic fragment ions is shown in FIG. 4 and results in the same dynamic range of 100:1 but the concentration range is shifted by an order of magnitude to higher concentrations.

FIG. 4A shows a corresponding response versus concentration curve for an ADC based detection system. For the weakest intensity species of fragment ion the linear range is still two orders of magnitude but is now shifted to a higher concentration range.

FIG. 5 illustrates a method of calibrating or quantitating an analyte sample according to a preferred embodiment. In particular, FIG. 5 shows the benefit of using a combination of two different species of characteristic fragment ions which are preferably present at different concentrations in order to calibrate the mass spectrometer or to quantitate an analyte sample.

With reference to FIG. 5, the most intense species of characteristic fragment ions may be used to calibrate or to quantitate an analyte of interest for responses in the range of 100 to 10,000 ions striking the ion detector per chromatographic ion peak whereas the weakest intensity species of characteristic fragment ions may be used to extend the dynamic range and to quantitate the analyte of interest when the response of the most intense species of characteristic fragment ions is greater than 10,000.

As a result, a ×10 fold increase in dynamic range may be obtained according to the preferred embodiment.

Figure 5A:
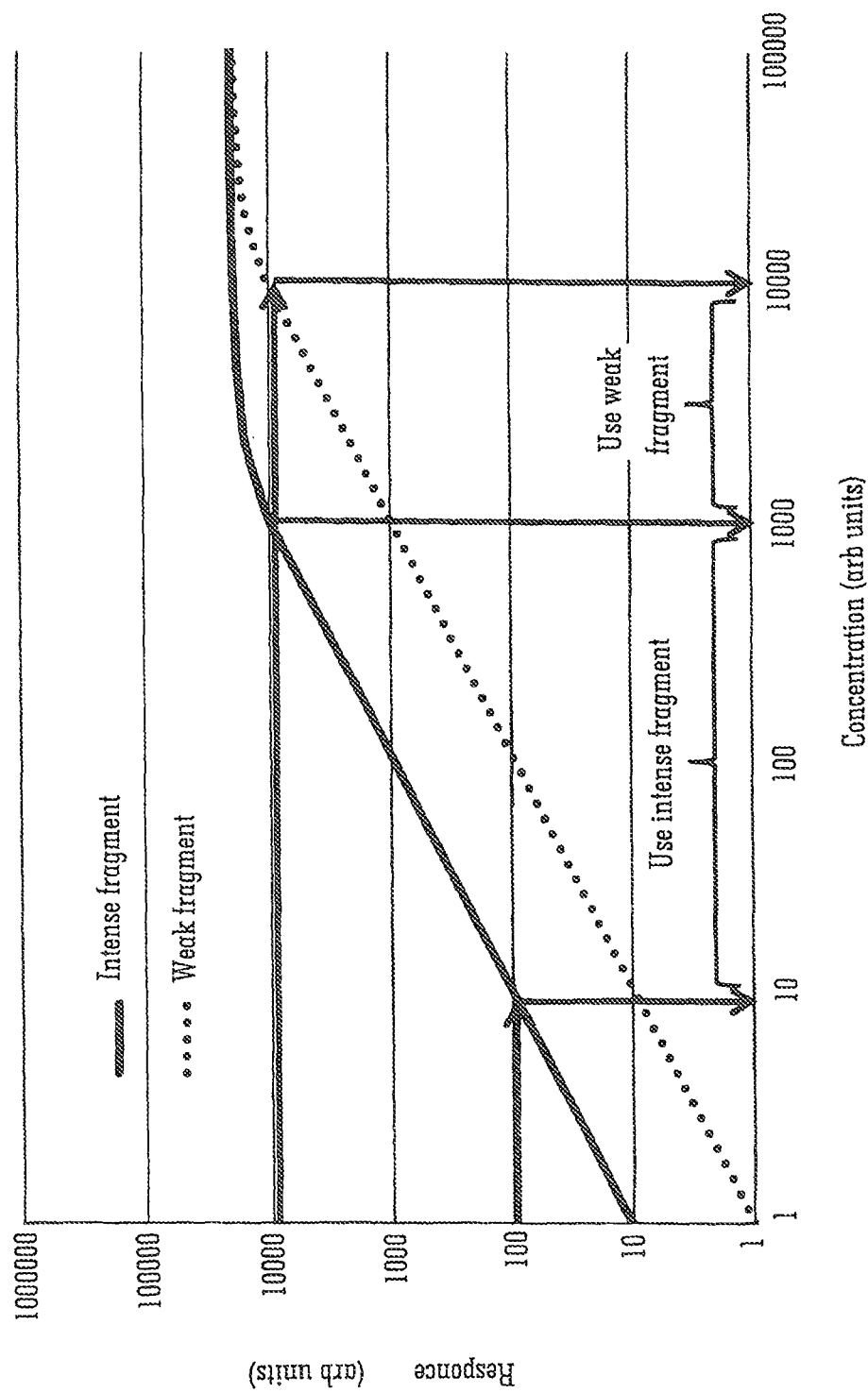

FIG. 5A shows a response versus concentration curve for an ADC based detection system and indicates how the ion detector saturates when more than 10,000 ions strike the ion detector per chromatographic peak. It is apparent from FIG. 5A that according to the preferred embodiment a sample can now be quantitated across three orders of magnitude of concentration (in contrast to the conventional approach which is only able to quantitate across two orders of magnitude).

It is apparent that choosing which characteristic fragment ions to use in order to quantitate an analyte of interest depending on which characteristic fragment ions are in the linear response region can lead to an order of magnitude increase in the dynamic range.

The present invention therefore results in a significant improvement in dynamic range compared with conventional approaches to quantitating an analyte sample.

In addition to choosing different characteristic fragment ion based detection limits or saturation limits it is recognised that other criteria may be used when determining the choice of characteristic fragment ion such as interferences, number of ions required to achieve a certain mass precision and which fragment ions to sum to give better detection limits.

According to an important further embodiment different isotope peaks of the same species of parent ions may be used as reference points for quantitation rather than using characteristic fragment ions. A related embodiment will be described in more detail below with reference to FIGS. 6 and 7.

According town embodiment the approach as described above is also applicable to other experiments such as Selected on Recording ("SIR"). In these experiments a mass filter is not required prior to a mass analyser. Quantitation is performed using precursor ions or fragment ions created within the ion source, or during the ionization process. Alternatively, a fragmentation device may be provided between the ion source and the mass analyser to produce characteristic fragment or product ions.

According to an embodiment selection of which characteristic ions to use in order to provide quantitation of an analyte sample may be implemented as part of a post acquisition or post processing routine. Alternatively, the choice of which characteristic on to use in order to provide quantitation be implemented in real time on a spectra by spectra basis including on a push by push basis.

According to an embodiment the preferred method of quantitation may be implemented on other mass analysers such as an Orbitrap® mass spectrometer, a FT-ICR mass spectrometer and a quadrupole mass analyser.

According to an embodiment the preferred approach may be used in conjunction with Time of Right modes such as Enhanced Duty Cycle ("EDC") and high Duty Cycle ("HDC").

According to an embodiment the preferred approach may be used with different detection schemes such as Analogue to Digital Converters ("ADCs") including multistage and non linear ADCs and Time to Digital Converters ("TDCs").

According to an embodiment the preferred approach may be used to compensate for detector saturation as well as ADC or TDC saturation.

According to an embodiment only data associated with the range of characteristic fragment ions is preferably stored.

According to an embodiment mass spectral data may not be stored mimicking the traditional data format of intensity versus time associated with MRM or SIR.

According to an embodiment the chosen or characteristic fragment or other ions may also be used for non-quantitative reasons such as determining isotope or fragment ion ratios and may be used for confirmatory purposes.

According to an embodiment the chosen or characteristic ions may be used for quantitative reasons with an additional confirmatory check of isotope or fragment ion ratios.

Figure 6:
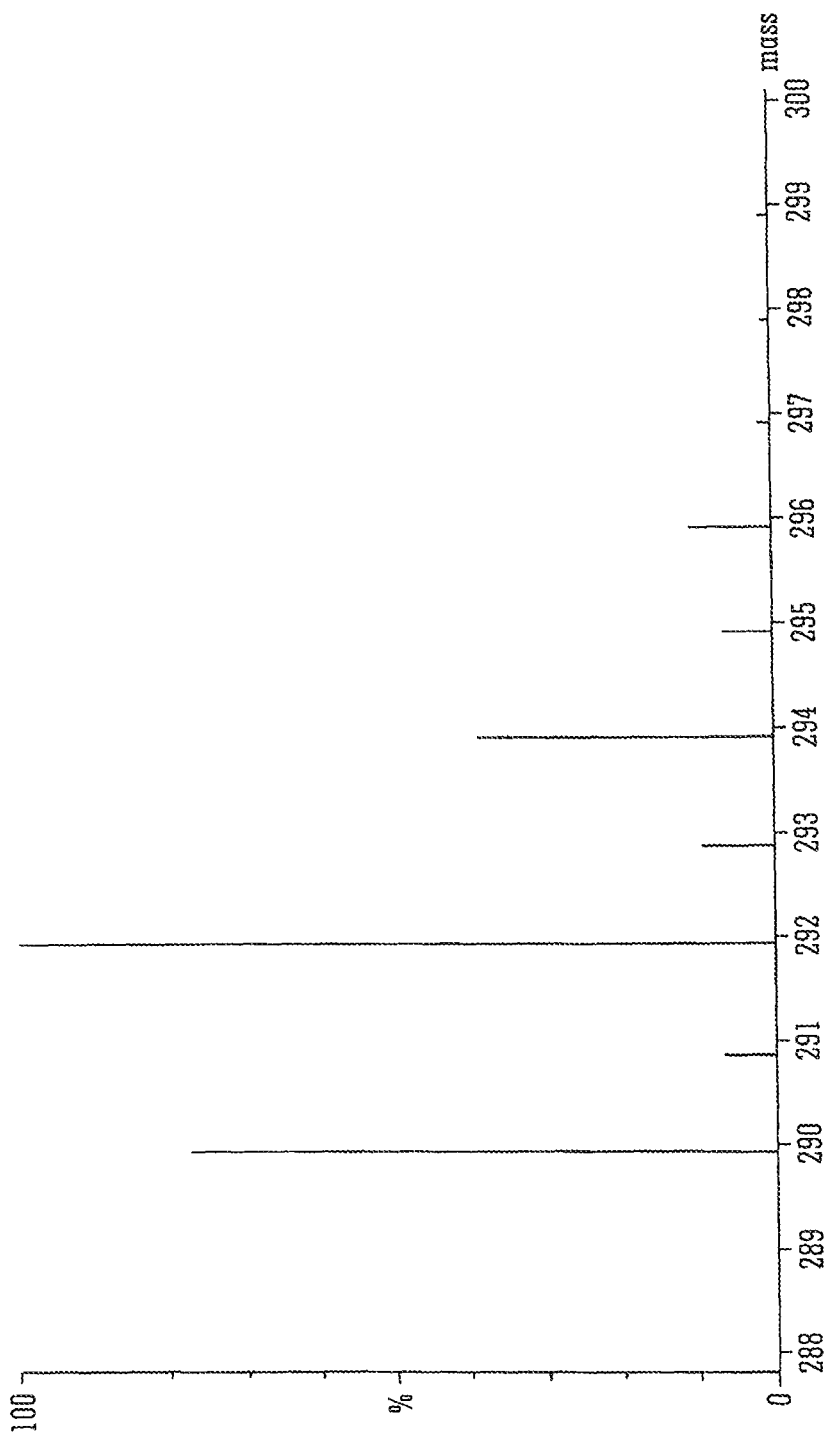
FIG. 6 shows detail of a mass spectrum of a target compound of interest having ten isotopes.

In another embodiment the objective of the analysis may be to quantify the amount of a target compound and then obtain confirmatory isotopic ratios. An example of a mass spectrum of a target compound containing 10 isotopes is shown in FIG. 6. The isotopes have nominal masses of 290, 291, 292, 293, 294, 295, 296, 297, 298 and 299. The most intense isotope has a nominal mass of 292, the second most intense isotope has a nominal mass of 290, the third most intense isotope has a nominal mass of 294 and the weakest intensity isotope has a nominal mass of 299.

A compound containing ten isotopes I1, I2, I3, I4, I5, I6, I7, I8, I9, I10 will have 45 different possible isotopic ratios (i.e. I1:I2 I1:I3 I1:I4 etc,). The 45 different isotopic ratios act like a unique fingerprint and determination of the various isotopic ratios enables accurate confirmation of the presence of a target compound of interest.

The 45 different possible isotopic ratios for the compound of interest which was analysed and shown in FIG. 6 were ranked by order of their detection probability and are shown in FIG. 7. The acceptability of each of the 45 isotopic ratios are shown for three samples (A, B and C) of increasing concentration.

The weakest analyte sample (A) only has acceptable ratios for the first three isotopic ratios (I3:I1 I3:I5 I1:I5) because only the three most abundant isotopes (having nominal masses of 290, 292 and 294) were above the lower detection limit.

The second analyte sample (B) having a medium or intermediate concentration shows acceptable ratios for all 45 possible isotopic ratios.

The most concentrated or highest concentration analyte sample (C) results in detector saturation for many of the isotopic ratios and hence the ratios based on the most abundant ions will be in error. However, the weaker isotopes are within the dynamic range of the mass spectrometer and overall 15 isotopic ratios are found to be acceptable.

It is therefore possible to extend the dynamic range of the analysis according to a preferred embodiment of the present invention by selecting isotopes which are within the dynamic range of the Time of Flight mass spectrometer when compared to the selection of any one isotopic ratio.

Various further embodiments are contemplated. According to an alternative less preferred embodiment a Time of Flight mass spectrometer is not essential to the present invention. The approach to quantitation as described above may also be utilised with other types of mass spectrometers and separation devices such as ion mobility spectrometers ("IMS"), differential mobility spectrometers ("DMS") and Field Asymmetric ion Mobility Spectrometry ("FAIMS") devices.

The information gathered from the characteristic fragment ions can also be used to control an instrument parameter such as collision energy or ionization efficiency, ion transmission or detector gain so as to improve the dynamic range.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
   determining the intensity of an analyte by determining the intensity of first characteristic ions when the intensity of said first characteristic ions is within a first range;
   determining the intensity of said analyte by determining the intensity of second different characteristic ions when the intensity of said first characteristic ions is outside of said first range; and
   determining one or more isotope or fragment ion ratios of said analyte using said first characteristic ions or said second characteristic ions based on whether the intensity of said first characteristic ions is within said first range in order to confirm the identity of said analyte or to identify said analyte.

2. A method as claimed in claim 1, wherein said first characteristic ions comprise fragment, product or adduct ions derived from said analyte.

3. A method as claimed in claim 1, wherein said first characteristic ions comprise one or more first isotopes of said analyte.

4. A method as claimed in claim 1, wherein said second characteristic ions comprise fragment, product or adduct ions derived from said analyte.

5. A method as claimed in claim 1, wherein said second characteristic ions comprise one or more second isotopes of said analyte.

6. A method as claimed in claim 1, wherein said first range substantially corresponds with the detection or unsaturated range of an ion detector.

7. A method as claimed in claim 1, wherein when the intensity of said first characteristic ions is outside of said first range the intensity of said second different characteristic ions is still substantially within the detection or unsaturated range of an ion detector.

8. A method as claimed in claim 1, wherein the step of determining one or more isotope ratios of said analyte comprises:
   determining one or more first isotope ratios by analysing a first sample comprising a first concentration of the analyte; and
   determining one or more second different isotope ratios by analysing a second different sample comprising a second different concentration of said analyte.

9. A method as claimed in claim 1, further comprising controlling an instrument parameter of a mass spectrometer based upon a determination of the intensity or other property of said first characteristic ions or the intensity or other property of said second characteristic ions.

10. A method as claimed in claim 9, wherein said instrument parameter comprises: (i) a collision or fragmentation energy; (ii) an ionisation efficiency; (iii) an ion transmission efficiency; or (iv) an ion detector gain.

11. A method as claimed in claim 1, further comprising:
    separating parent or fragment ions according to a physico-chemical property.

12. A method as claimed in claim 11, wherein said physico-chemical property comprises ion mobility, differential ion mobility, mass, mass to charge ratio or time of flight.

13. A method as claimed in claim 1, wherein said method comprises a method of Multiple Reaction Monitoring ("MRM").

14. A method as claimed in claim 1, wherein parent analyte ions are selected or isolated by a mass filter.

15. A method as claimed in claim 14, wherein said parent analyte ions selected or isolated by said mass filter are fragmented or reacted to form said first characteristic ions or said second characteristic ions.

16. A method as claimed in claim 1, wherein the step of determining the intensity of said first characteristic ions comprises mass analysing said first characteristic ions.

17. A method as claimed in claim 1, wherein the step of determining the intensity of said second characteristic ions comprises mass analysing said second characteristic ions.

18. A method as claimed in claim 16, wherein the step of mass analysing said first or second characteristic ions comprises mass analysing said first or second characteristic ions using an axial acceleration or orthogonal acceleration Time of Flight mass analyser.

19. A method as claimed in claim 1, wherein said first and second characteristic ions have different masses or different mass to charge ratios or different chemical structures or different number of neutrons or one more different physico-chemical properties.

20. A mass spectrometer comprising:
    a control system arranged and adapted:

(i) to determine the intensity of an analyte by determining the intensity of first characteristic ions when the intensity of said first characteristic ions is within a first range;
(ii) to determine the intensity of said analyte by determining the intensity of second different characteristic ions when the intensity of said first characteristic ions is outside of said first range; and
(iii) to determine one or more isotope or fragment ion ratios of said analyte using said first characteristic ions or said second characteristic ions based on whether the intensity of said first characteristic ions is within said first range in order to confirm the identity of said analyte or to identify said analyte.

21. A mass spectrometer as claimed in claim 20, further comprising a separator for separating parent or fragment ions according to a physico-chemical property.

22. A mass spectrometer as claimed in claim 21, wherein said separator comprises an ion mobility, differential ion mobility, mass, mass to charge ratio or time of flight separator.

23. A mass spectrometer as claimed in claim 20, wherein said control system is arranged and adapted to perform a Multiple Reaction Monitoring ("MRM") analysis.

24. A mass spectrometer as claimed in claim 20, further comprising a mass filter for selecting or isolating parent analyte ions.

25. A mass spectrometer as claimed in claim 24, further comprising a fragmentation or reaction device wherein said parent analyte ions selected or isolated by said mass filter are fragmented or reacted, in use, within said fragmentation or reaction device to form said first characteristic ions or said second characteristic ions.

26. A mass spectrometer as claimed in claim 20, further comprising a mass analyser for mass analysing said first or second characteristic ions and determining the intensity of said first or second characteristic ions.

27. A mass spectrometer as claimed in claim 26, wherein said mass analyser comprises an axial acceleration or orthogonal acceleration Time of Flight mass analyser.

28. A mass spectrometer as claimed in claim 20, wherein said first and second characteristics ions have different masses or different mass to charge ratios or different chemical structures or different number of neutrons or one or more different physico-chemical properties.

29. A method of mass spectrometry comprising:
determining one or more first isotope ratios by analysing a first sample comprising a first concentration of an analyte;
determining one or more second different isotope ratios by analysing a second different sample comprising a second different concentration of said analyte; and
selecting one or more of said one or more first isotope ratios or said one or more second isotope ratios to use to confirm the identity of said analyte or to identify said analyte based on whether an isotope intensity used to determine said one or more first isotope ratios or said one or more second isotope ratios is within a first range.

30. A mass spectrometer comprising:
a control system arranged and adapted:
(i) to determine one or more first isotope ratios by analysing a first sample comprising a first concentration of an analyte;
(ii) to determine one or more second different isotope ratios by analysing a second different sample comprising a second different concentration of said analyte; and
(iii) to select one or more of said one or more first isotope ratios or said one or more second isotope ratios to use to confirm the identity of said analyte or to identify said analyte based on whether an isotope intensity used to determine said one or more first isotope ratios or said one or more second isotope ratios is within a first range.

* * * * *